United States Patent [19]

Misra et al.

[11] Patent Number: 4,883,811

[45] Date of Patent: Nov. 28, 1989

[54] 7-OXABICYCLOHEPTANE IMINO INTERPHENYLENE SUBSTITUTED PROSTAGLANDIN ANALOGS USEFUL IN THE TREATMENT OF THROMBOTIC DISEASE

[76] Inventors: Raj N. Misra, 12 Eaton Pl., Hopewell, N.J. 08525; Steven E. Hall, 57 Colleen Cir., Trenton, N.J. 08638

[21] Appl. No.: 272,373

[22] Filed: Nov. 17, 1988

[51] Int. Cl.$^4$ ............... A61K 31/34; C07D 307/00
[52] U.S. Cl. ........................ 514/469; 549/463
[58] Field of Search ............... 549/463; 560/57, 64, 560/53; 514/469

[56] References Cited

U.S. PATENT DOCUMENTS

| | | | |
|---|---|---|---|
| 4,416,896 | 11/1983 | Nakane et al. | 549/463 |
| 4,418,076 | 11/1983 | Nakane et al. | 549/463 |
| 4,463,015 | 7/1984 | Haslanger et al. | 549/463 |
| 4,474,804 | 10/1984 | Das et al. | 549/463 |
| 4,522,949 | 6/1985 | Das et al. | 549/463 |
| 4,535,513 | 8/1985 | Das et al. | 549/463 |

*Primary Examiner*—Mary C. Lee
*Assistant Examiner*—Bernard I. Dentz
*Attorney, Agent, or Firm*—Burton Rodney

[57] ABSTRACT

7-Oxabicycloheptane imino interphenylene substituted prostaglandin analogs are provided having the structural formula

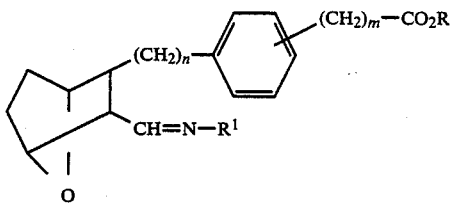

wherein n is 1 or 2; m is 1 or 2; R is H, lower alkyl, or alkali metal; and $R^1$ is $-OR^2$,

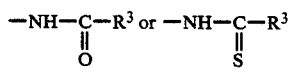

where $R^2$ is lower alkyl, aryl, aralkyl, cycloalkylalkyl, alkanoyl or aroyl; and $R^3$ is lower alkyl, aryl, aralkyl, alkoxy, aryloxy, aralkoxy, $-$NHaralkyl, $-$NHalkyl, $-$NHalkylcycloalkyl or $-$NHaryl.

These compounds are cardiovascular agents which exhibit thromboxane antagonist activity and thus are useful in the treatment of thrombotic and vasospastic disease.

20 Claims, No Drawings

7-OXABICYCLOHEPTANE IMINO INTERPHENYLENE SUBSTITUTED PROSTAGLANDIN ANALOGS USEFUL IN THE TREATMENT OF THROMBOTIC DISEASE

DESCRIPTION OF THE INVENTION

The present invention relates to 7-oxabicycloheptane substituted prostaglandin analogs which are cardiovascular agents useful, for example, in the treatment of thrombotic disease or vasospastic disease. These compounds have the structural formula

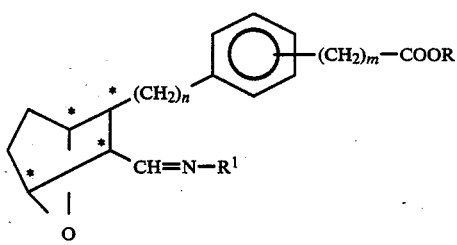

and including all stereoisomers thereof, wherein n is 1 or 2; m is 1 or 2; R is H, alkali metal or lower alkyl; and $R^1$ is $-OR^2$,

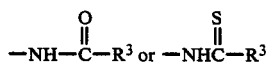

wherein $R^2$ is lower alkyl, aryl, aralkyl, cycloalkylalkyl, alkanoyl or aroyl, and $R^3$ is lower alkyl, aryl, aralkyl, alkoxy, aryloxy, aralkoxy, alkylamino, arylamino, cycloalkylalkylamino or aralkylamino Thus, the compounds of the invention encompass the following types of compounds:

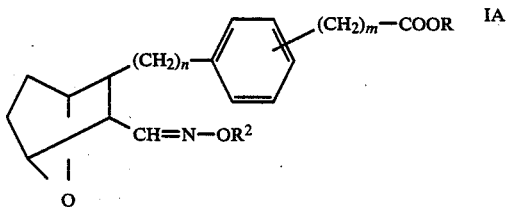

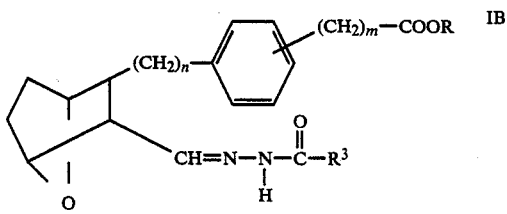

and

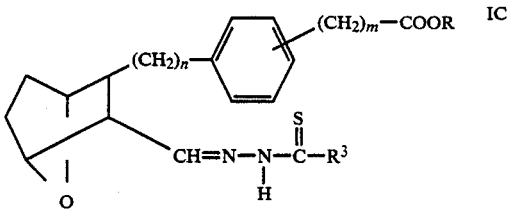

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 to 2 lower alkyl groups, 1 or 2 halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine, with chlorine being preferred.

The term "alkanoyl" refers to lower alkyl linked to a carbonyl (CO).

The term "aroyl" refers to aryl linked to a carbonyl (CO).

Preferred are those compounds of formula I wherein n is 1, m is 1, R is H, $R^1$ is

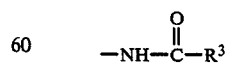

where $R^3$ is phenylamino, alkylamino, aralkylamino or cycloalkylalkylamino and the $(CH_2)_m$—COOR group is in the ortho or meta position.

The various compounds of the invention may be prepared as described below.

Bromophenylalkyl alcohol <u>A</u>

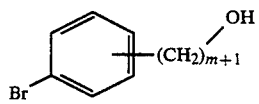   A wherein m is 1 or 2 is treated with a protecting compound such as chloro-t-butyldimethylsilane, employing conventional procedures, to form the protected bromophenalkyl compound B

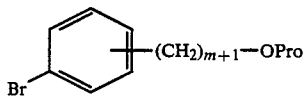   B wherein Pro represents a protecting group

Examples of protecting compounds suitable for use herein in reacting with bromophenalkyl alcohol A include but are not limited to

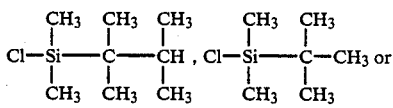

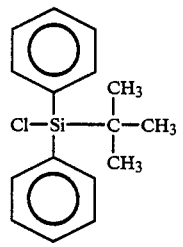

The protected compound B is then transmetallated by treatment with t-C₄H₉Li or n-C₄H₉Li in the presence of ethyl ether at reduced temperature of from about −100° to about 0° C. (or is subjected to a Grignard reaction by treatment with magnesium in the presence of an inert organic solvent such as tetrahydrofuran (THF) or ethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

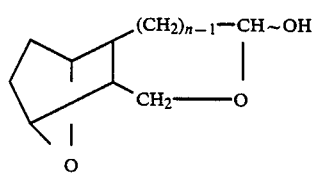   C employing a molar ratio of C:B of within the range of from about 1:2 to about 1:3, in the presence of an inert organic solvent such as THF at a reduced temperature of from about −78 to about 0° C., to form the condensed 7-oxabicycloheptane compound II

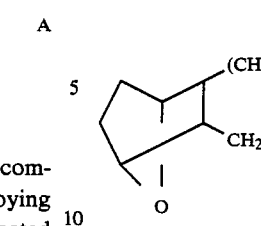   II

The condensed compound II is then subjected to hydrogenolysis by treatment with hydrogen in the presence of a catalyst such as palladium on charcoal in acetic acid or an inert organic solvent such as methylacetate containing 1–3% of perchloric acid, to form the alcohol III

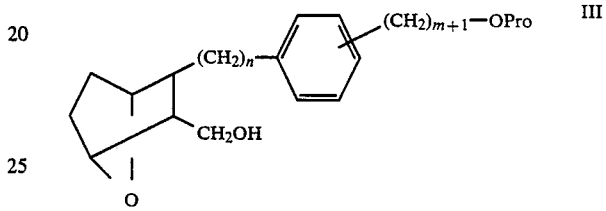   III which is protected by treatment with, for example, a solution of acetic anhydride, pyridine and 4-dimethylaminopyridine in dry methylene chloride to form the protected alcohol IV

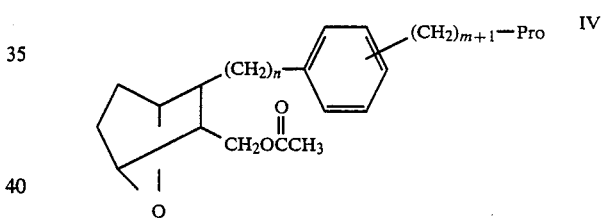   IV

Alternatively, compound II can be protected by treatment with, for example, a solution of acetic anhydride and pyridine to form compound II′

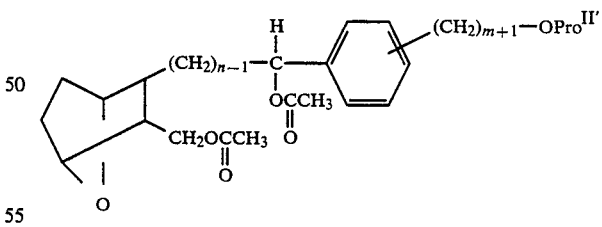   II′ which is then subjected to hydrogenolysis as described above to provide compound IV.

The protected alcohol IV is then subjected to a Jones oxidation wherein a solution of protected alcohol IV in acetone cooled to from about −10° to about 25° C. is treated with Jones reagent (that is, CrO₃ dissolved or suspended in sulfuric acid in the presence of water, prepared as described in Fieser and Fieser, "Reagents for Organic Synthesis," Vol. 1 p. 142 (1967) to form crude acid which is deprotected by reaction with aqueous hydroxide in the presence of inert organic solvent such as THF and then esterified, for example, by treatment with diazoalkane, such as diazomethane, to form the alcohol ester V

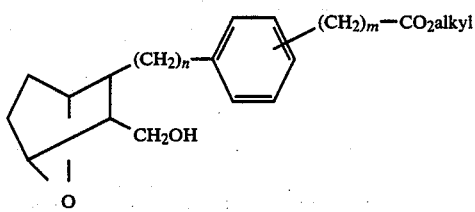

Next, the alcohol ester V is subjected to a Dess-Martin oxidation wherein a solution of alcohol ester V in methylene chloride is added to a mixture of Dess-Martin periodinane in dry methylene chloride to form the aldehyde VI

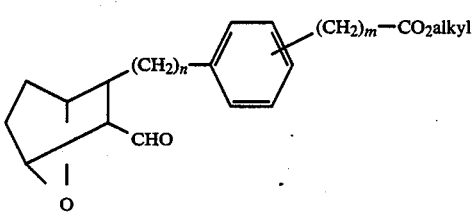

Alternatively, addition of V in methylene chloride to pyridinium chlorochromate in the presence of sodium acetate in methylene chloride also forms aldehyde VI.

The aldehyde VI is then used to prepare the imine compounds of the invention.

Compounds of the invention where $R^1$ is $-OR^2$ may be prepared by reacting aldehyde VI with an oxyamine, such as of the structure D $$H_2NOR^2 \qquad D$$

in a protic solvent such as methanol or ethanol, employing a molar ratio of aldehyde VI: D within the range of from about 0.8:1 to about 1:1 to form ester ID

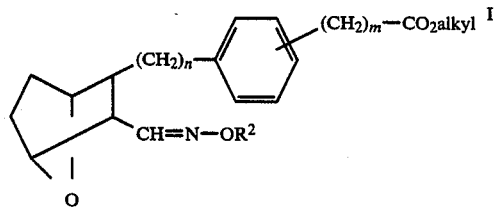

Compounds of the invention where $R^1$ is

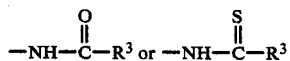

may be prepared by reacting aldehyde VI with a hydrazine derivative E or F

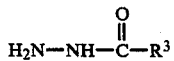

or

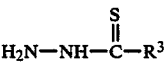

in a protic solvent such as methanol or ethanol, to form compound IE or IF, employing a molar ratio of VI:E or F of within the range of from about 0.8:1 to about 1:1.

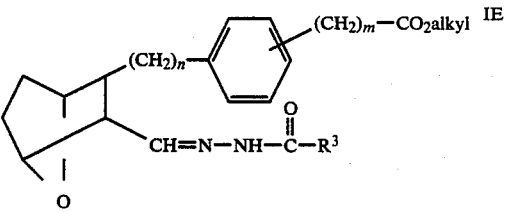

or

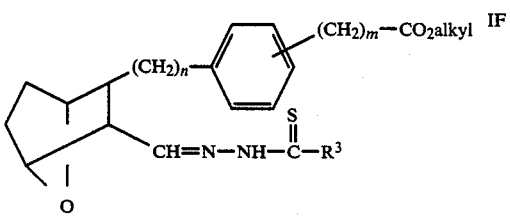

The esters ID, IE and IF can be converted to the corresponding alkali metal salt (where R is Na, K or Li) by treating the esters with an alkali metal hydroxide such as NaOH, KOH or LiOH. The corresponding acid may be formed by treating the alkali metal salts with an acid such as dilute hydrochloric acid or oxalic acid.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared by employing starting materials and following the procedure as outlined in U.S. Pat. No. 4,143,054. Examples of such stereoisomers are set out below.

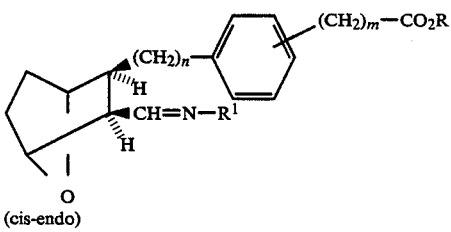
(cis-endo)

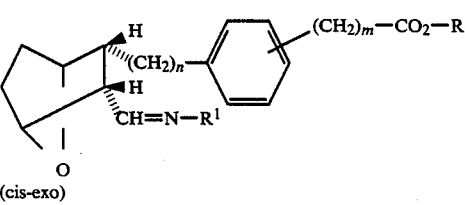
(cis-exo)

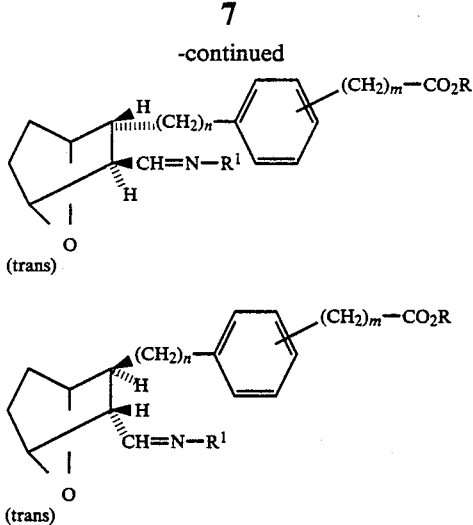

The nucleus in each of the compounds of the invention is depicted as

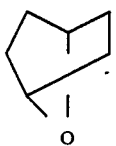

for matter of convenience; it will also be appreciated that the nucleus in the compounds of the invention may be depicted as

The compounds of this invention are cardiovascular agents useful as platelet aggregation inhibitors, e.g., for treatment of thrombotic disease, such as coronary or cerebral thromboses. In addition, the compounds of the invention are useful in inhibiting bronchoconstriction such as associated with asthma and airways hyper reactivity. They are also selective thromboxane A₂ receptor antagonists, e.g., having a vasodilatory effect for treatment of myocardial ischemic disease, such as angina pectoris.

In addition, the compounds of the invention may be useful in improving post-ischemic myocardial dysfunction, for example, decreased contractile dysfunction, decrease in tissue necrosis, and decrease in infarct size, preventing or treating toxemia in pregnancy, preventing or reducing platelet loss during extracorporeal circulation, potentiating iuretic-induced diuresis, preventing or reducing adverse reactions to protamine, preventing nephrotoxicity of drugs such as cyclosporine A, gentamycin and the like, preventing thrombosis and adverse reactions to radiographic contrast agents, preventing or reducing venous thrombosis (in conjunction with heparin), treating burn injury and promoting wound healing, treating ischemia (alone or in combination with a calcium channel blocker), preserving vascular patency and circulation during and following vascular surgery, preventing reperfusion injury after CNS ischemic states like stroke or vascular surgery, treating tardive dyskenesia, treating Raynaud's disease, treating unstable angina, treating purpura fulminarus, and treating thrombotic thrombocytopenia purpura. Furthermore, the compounds of the invention may be useful in the treatment of pulmonary embolism, diabetic retinopathy, and in coronary artery by-pass, renal dialysis, thrombolysis, endarterectomy, acute renal failure, lupus, peripheral vascular disease, intermittent claudication, pulmonary hypertension after mitral valve surgery, pulmonary hypertension after intralipid infusion, subarachnoid hemorrhage, treating or preventing complications following organ transplant (particularly cardiac or renal), treating persistent pulmonary hypertension of the newborn, treating tuberculosis and enhancing immune surveillance and promoting antibiotic penetration to sites of infection/abscess.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg (or from about 5 to about 2500 mg, preferably from about 10 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade.

EXAMPLE 1

[1S-(1α,2β,3β,4α)]-3-[[3-[[[(Phenylamino)carbonyl]hydrazono]methyl]-7-oxabicyclo]2.2.1]hept-2-yl]methyl]-benzene acetic acid

A. 3-Bromophenyloxythexyldimethylsilane

To a stirred solution of 3-bromophenylacetic acid (55.8 g, 260 mmol, Aldrich) under argon at 0° C. was added 1M B₂H₆/tetrahydrofuran (THF) solution dropwise (200 mL, 300 mmol) over one hour. This mixture was stirred at 0° C. for 5.5 hours and quenched slowly with water. The resulting mixture was concentrated in vacuo and partitioned between 300 mL of saturated NaHCO₃ solution and ethyl ether (4×40 mL). The combined ether extracts was dried (MgSO₄), filtered and concentrated in vacuo to give 51.7 g of crude alcohol. To a stirred solution of this alcohol and (C₂H₅)₃N (75 mL, 538 mmol) in 500 mL of dry CH₂Cl₂ under argon at 0° C. was added thexyldimethylsilyl chloride (56.2 mL, 286 mmol) over 15 minutes. The reaction mixture was stirred at 0° C. for 75 minutes and at room temperature for 15 hours. This mixture was diluted with 500 mL of ethyl ether and the precipitate was filtered off. The solid was rinsed with ethyl ether (3×300 mL).

The filtrate was concentrated in vacuo and partitioned between 300 mL of saturated NH₄Cl solution and ethyl ether (4×300 mL). The combined ether extracts was dried (MgSO₄), filtered and concentrated in vacuo. This crude product was distilled under pump vacuum at 148°–154° C. to give 76.9 g (87%) of desired title bromide. TLC=silica gel, 1:1 hexane-benzene, $R_f$ 0.87, Ce(SO₄)₂.

B.
[[1S-(1α,2β,3β,4α)]-2-[3-[[3-(Hydroxymethyl)-7-oxabicyclo[2.2.1]hept-2-yl]-hydroxymethyl]benzene]ethoxy]dimethyl-(1,1,2-trimethylpropyl)silane To a solution of 10.0 g (29.1 mmol) of Part A protected bromophenethyl compound in 60 mL of dry ethyl ether cooled to −78° was added dropwise 30 mL (1.7 m in pentane, 51 mmol, Aldrich) of t-butyllithium solution over ~15 minutes. The reaction mixture was stirred at −78° for 15 minutes then 0° for 30 minutes. The resulting anion solution was re-cooled to −78°, 40 mL of dry tetrahydrofuran was introduced and then a solution of 1.87 g (12.0 mmol) of (exo)octahydro-4,7-epoxyisobenzofuran-1-ol in 20 mL of tetrahydrofuran was added dropwise. A precipitate formed. After 15 minutes, the reaction was warmed to 0°, quenched after and additional 1 hour at 0° with 5 mL of water, then added to 200 mL of water and extracted with two-75 mL portions of ethyl acetate. The organic extracts were combined, dried (magnesium sulfate and concentrated in vacuo to give an oil. The crude oil was purified by flash chromatography (Merck silica, 23×5.0 cm, 1:4 ethyl acetate/petroleum ether then ethyl acetate) to afford 4.10 g (10.1 mmol, 85%) of title compound as a colorless oil.

C.
[[1S-(1α,2β,3β,4α)]-2-[3-[[3-(Hydroxymethyl)-7-oxabicyclo[2.2.1]hept-2-yl]-methyl]-benzene]ethoxy]-dimethyl-(1,1,2-trimethylpropyl)silane A mixture of 4.05 g (10.0 mmol) of Part B compound and 5.50 g of 10% palladium on activated carbon (Aldrich) in 80 mL of glacial acetic acid was shaken under an atmosphere of hydrogen (40 psi) on a Parr apparatus for 24 hours. The resulting mixture was passed through a polycarbonate filter to remove the catalyst and the filtrate was concentrated in vacuo to give an oil. The crude oil was partitioned between 100 mL of ethyl acetate and 100 mL of water. The organic layer was separated, dried (magnesium sulfate) and concentrated in vacuo to afford 3.72 g (9.60 mmol, 96%) of crude title alcohol as a colorless oil.

D.
[[1S-(1α,2β,3β,4α)]-2-[3-[[3-(Acetoxymethyl)-7-oxabicyclo[2.2.1]hept-2-yl]-hydroxymethyl]benzene]ethoxy]dimethyl-(1,1,2-trimethylpropyl)silane To a solution of 3.64 g (9.38 mmol) of Part C alcohol, 50 mg (0.41 mmol, Aldrich) of 4-dimethylaminopyridine, 1.4 mL of acetic anhydride and 1.2 mL of pyridine in 25 mL of dry methylene chloride was stirred at room temperature for 24 hours. The reaction mixture was partitioned between 50 mL of hexane and 50 mL of 1M aqueous HCl solution. The organic layer was separated, dried (magnesium sulfate) and concentrated in vacuo to give an oil. The crude oil was purified by flash chromatography (Merck silica, 20×4.0 cm, 1:8 ethyl acetate/petroleum ether) to afford 3.00 g (6.98 mmol, 74%) of title compound as a colorless oil.

E.
Methyl[1S-(1α,2β,3β,5α)]3-[[3-(formyl)-7-oxabicyclo[2.2.1]hept-2-yl]methyl]-benzene acetate To a solution of 2.90 g (6.74 mmol) of Part D compound in 60 mL of reagent acetone cooled in an ice-bath was added rapidly 10 mL (2.6 m in Cr⁺⁶, 26 mEg, prepared as described in Fieser and Fieser, "Reagents for Organic Synthesis", Vol I, p. 142, (1967) of Jones reagent. The reaction mixture was stirred at 0° for 2 hours, then quenched by the addition of 5 mL of isopropanol and warmed to room temperature for 30 minutes. The resulting green slurry was filtered through a pad of Celite. The filtrate was concentrated in vacuo and the residue partitioned between 50 mL of water and 50 mL of ethyl acetate. The organic layer was separated and the aqueous was extracted with an additional 50 mL of ethyl acetate. The organic extracts were combined, dried (magnesium sulfate) and concentrated in vacuo to give the crude acid as an oil. The crude acid was stirred with 40 mL of 1:1 tetrahydrofuran/1M aqueous NaOH at room temperature for 2 hours to cleave the acetate. The resulting solution was cooled in an ice-beth, acidified with 25 mL of 1M aqueous HCl solution, then extracted with two 50 mL portions of ethyl acetate. The organic extracts were combined, dried (magnesium sulfate) and treated at 0° with excess ethereal diazomethane (until a yellow color persisted). The excess diazomethane was quenched by dropwise addition of glacial acetic acid and the solution concentrated in vacuo to give an oil. The oil was purified by flash chromatography (Merck silica, 15×5.0, ethyl acetate) to afford 1.56 g (5.38 mmol, 80%) of title alcohol ester as a pale yellow oil.

F. Methyl-[1S-(1α,2β,3β,5α)]3-[[3-(formyl)-7-oxabicyclo[2.2.1]hept-2-yl]methyl]-benzeneacetate To a mixture of 950 mg (2.24 mmol, Aldrich) of Dess-Martin periodinane in 10 mL of dry methylene chloride was added rapidly at room temperature a solution of 500 mg (1.72 mmol) of Part E of alcohol ester in 5 mL of methylene chloride. The reaction mixture was stirred for 30 minutes, then 75 mL of ethyl ether was added followed by 50 mL of saturated aqueous sodium bicarbonate solution containing 2.7 g (17 mmol) of sodium thiosulfate. The mixture was stirred rapidly for 15 minutes, then the resulting clear organic layer was separated, washed with 40 mL of saturated aqueous sodium bicarbonate solution, 50 mL of brine, dried (magnesium sulfate) and concentrated in vacuo to afford 470 mg (163 mmol, 95%) of crude title aldehyde as an oil.

G.
[1S-(1α,2β,3β,4α)]-3-[[3-[[[(Phenylamino)carbonyl]hydrazona]methyl]-7-oxabicyclo[2.2.1]hept-2-yl]methyl]-benzene acetic acid, methyl ester A mixture of 450 mg (1.56 mmol) of Part F aldehyde and 260 mg (1.72 mmol, Alfa) of 4-phenylsemicarbazide in 3 mL of dry methanol (Burdick and Jackson) was stirred at room temperature for 16 hours. The resulting solution was concentrated in vacuo to give a foam. The crude material was purified by flash chromatography (Merck silica, 15×3.0 cm, 2:1 ethyl acetate/petroleum ether) to afford 597 mg (1.42 mmol, 91%) of syn/anti imino ester as a white solid foam.

H.
[1S-(1α,2β,3β,4α)]-3-[[3-[[[(Phenylamino)carbonyl]hydrazona]methyl]-7-oxabicyclo[2.2.1]hept-2-yl]methyl]-benzene acetic acid A solution of 550 mg (1.31 mmol) of Part G ester and 82 mg (1.96 mmol, Aldrich) of lithium hydroxide monohydrate in 9 mL of 2:1 tetrahydrofuran/water was stirred rapidly at room temperature for 16 hours. The reaction mixture was acidified (pH=1) by addition of 2.1 mL of 1M aqueous HCl, then added to 25 mL of water and extracted with 20 mL of ethyl acetate. The organic extract was separated, dried, (magnesium sulfate) and concentrated in vacuo to afford 525 mg (1.29 mmol, 98%) of title compound as a white solid foam.

IR (KBr): 3700–2700 (broad), 1701, 1595, 1538, 1448, 755 cm$^{-1}$.

270 MHz $^1$H NMR (CDCl$_3$): 0.85–1.85 (m, 4H), 2.05–2.65 (m, 3H), 2.74, 2.93 (dd, J=8, 8 and m for anti/syn isomers, ~7:3, 1H total), 3.58 (s, 2H, —CH$_2$—COOH), 4.18, 4.33 (d, J=5 and d, J=4 for syn/anti isomers, ~3:7, 1H total, bridgehead), 4.39, 4.53 (d, J=5 and d, J=4 for syn/anti isomers, ~3:7, 1H total, bridgehead), 6:53 (d, J=8, for syn isomer, ~0.3H, —CH=C—), 6.90–7.55 (m, 9H), 7.94, 8.21 (pair of singlets for anti/syn isomers, ~7:3, 1H total, —NH—), 9.81, 10.41 (pair of singlets for anti/syn isomers, ~7:3, 1H total, —NH—).

Partial 67.5 MHz $^{13}$CNMR (CDCl$_3$): 78.6, 79.4, 79.9, 79.0, 119.7, 119.8, 134.2, 134.4, 137.3, 137.6, 140.8, 140.9, 146.1, 146.2, 154.6, 155.6, 176.1, 176.6.

MS(CI): 408 (M+H)$^+$.

TLC: R$_f$ (silica gel, 1:9 methanol/methylene chloride)=0.34, ammonium molybdate/ceric sulfate, UV, homogeneous.

Analysis Calculated for C$_{23}$H$_{25}$N$_3$O$_4$: C, 67.79; H, 6.18; N, 10.32. Found: C, 67.66; H, 6.22; N, 10.97.

EXAMPLE 2
[1S-(1α,2β,3β,4α)]-3-[2-[3-[[[(Phenylamino)-carbonyl]hydrazono]methyl]-7-oxabicyclo-[2.2.1]hept-2-yl]ethyl]benzeneacetic acid

A.
[1S-(1α,2β,3β,4α)]-2-[3-[2-[3-(Hydroxymethyl)-7-oxabicyclo[2.2.1]-hept-2-yl]-1-hydroxyethyl]benzene]ethoxydimethyl-(1,1,2-trimethylpropyl)silane To a stirred mixture of magnesium turnings (5.77 g, 237 mmol) and iodine (few crystals) in 70 mL of dry tetrahydrofuran under argon at 50° C. was added 5% of a solution of Example 1, Part A bromide (20.7 g, 60.3 mmol) in 120 mL of dry tetrahydrofuran. The remaining 95% of the bromide solution was added dropwise over 40 minutes after the I$_2$ color of the reaction mixture dissipated. The mixture was heated at 50° C. for 90 minutes and cooled to 0° C. To this 0° C. mixture was added a solution of (exo)octahydro-5-8-epoxy-1H-benzopyran-3-ol (3.00 g, 17.9 mmol) in 75 mL of dry tetrahydrofuran over 20 minutes. The reaction mixture was stirred at 0° C. for 30 minutes and at room temperature for 3 hours. The reaction mixture was quenched at 0° C. by a dropwise addition of 50 mL of CH$_3$OH and the magnesium turnings were filtered off through a pad of glass wool. The filtrate was concentrated in vacuo and partitioned between 100 mL of saturated NH$_4$Cl solution and ethyl acetate (3×150 mL). The combined ethyl acetate extracts was dried (MgSO$_4$), filtered, and concentrated in vacuo. Purification was affected by flash chromatography on 180 g Merck silica gel 60 using 3% CH$_3$OH in CH$_2$Cl$_2$ as eluant to give 7.52 g (95%) of title diol.

TLC=silica gel, 6% CH$_3$OH/CH$_2$Cl$_2$, R$_f$ fast moving isomer (F.M.I.), 0.66; slow moving isomer (S.M.I.), 0.63, Ce(SO$_4$)$_2$.

B.
[1S-(1α,2β,3β,4α)]-3-[2-[3-(Acetoxymethyl)-7-oxabicyclo[2.2.1]hept-2-yl]-1-acetoxyethyl]benzene acetic acid, methyl ester To a stirred solution of Part A diol (7.39 g, 17.1 mmol) in pyridine (7.51 mL, 103 mmol) under argon at 0° C. was added acetic anhydride (4.85 mL, 51.3 mmol) over 10 minutes. This mixture was stirred at 0° C. for one hour and at room temperature for 16 hours. The reaction mixture was diluted with 400 mL of ethyl ether and washed with 1N aqueous HCl solution (3×100 mL). The ethyl ether layer was dried (MgSO$_4$), filtered and concentrated in vacuo. The residue was dissolved in 100 mL of acetone and treated with Jones reagent until an orange red color persisted. The mixture was stirred at room temperature for 1 hour and quenched with isopropyl alcohol. The mixture was concentrated in vacuo and partitioned between 150 mL of H$_2$O and ethyl acetate (4×150 mL). The combined ethyl acetate extracts was washed with H$_2$O (2×50 mL), dried (MgSO$_4$), filtered and concentrated in vacuo. The crude acid was dissolved in 100 mL of ethyl ether and treated with ethereal CH$_2$N$_2$. The resulting yellow mixture was stirred at room temperature for 1 hour and the excess CH$_2$N$_2$ was destroyed by the addition of glacial acetic acid. The mixture was concentrated in vacuo and chromatographed on 200 g of Merck silica gel 60 using 2L of each 2:1 and 1:1 hexane-ether as eluent to give 5.50 g (83%) of title ester.

TLC: silica gel, 1:1 hexane-ether, R$_f$ 0.20, Ce(SO$_4$)$_2$.

C.
[1S-(1α,2β,3β,4α)]-3-[2-[3-(Acetoxymethyl)-7-oxabicyclo[2.2.1]hept-2-yl]-ethyl]benzene acetic acid, methyl ester To a stirred solution of Part A ester (5.40 g, 13.9 mmol) in 100 mL of methyl acetate under argon was added 2.5 mL of 70% aqueous HClO$_4$ and 0.54 g of 10% Pd/C. The atmosphere was replaced with hydrogen by several vacuum-fill cycles. The slurry was stirred at room temperature for 4 hours and the catalyst was filtered off through a 3″ pad of celite. The pad was rinsed with ethyl acetate (3×50 mL). The filtrate was concentrated to half volume and washed with saturated NH$_4$Cl solution (2×30 mL) and brine (1×50 mL). The organic layer was dried (MgSO$_4$), filtered and concentrated in vacuo. Purification was effected by flash chromatography on 200 g of Merck silica gel 60 using 2L of each of 2:1 and 1:1 hexane-ethyl ether as eluant to give 3.62 g of title acetate as an oil.

TLC: silica gel, 2% CH$_3$OH in CH$_2$Cl$_2$•R$_f$ 0.48, Ce(SO$_4$)$_2$.

D.
[1S-(1α,2β,3β,4α)]-3-[2-[3-(Hydroxymethyl)-7-oxabicyclo[2.2.1]hept-2-yl]-ethyl]benzene acetic acid, methyl ester To a stirred solution of Part C acetate (3.62 g, 10.5 mmol) in 100 mL of CH$_3$OH under argon at 0° C. was added t-C$_4$H$_9$OK (1.29 g, 11.5 mmol). The mixture was stirred at 0° C. for 15 minutes and at room temperature for 105 minutes. The mixture was concentrated in vacuo and partitioned between 100 mL of 0.1 N aqueous HCl solution and ethyl ether (3×100 mL). The combined ether extracts was dried (MgSO₄), filtered and concentrated in vacuo to give 3.06 g (96%) of title alcohol which was used for the next transformation without further purification.

TLC: silica gel, 4% $CH_3OH/CH_2Cl_2$•$R_f$ 0.54, Ce(SO₄)₂.

E.
[1S-(1α,2β,3β,4α)]-3-[2-[3-(Formyl)-7-oxabicyclo[2.2.1]hept-2-yl]ethyl]benzene acetic acid, methyl ester To a stirred slurry of 2.00 g (mmol) of pyridinium chlorochromate (PCC), 2.00 g Celite (dried at 120° C. for 4 hours), and 0.20 g of anhydrous Na acetate in 20 mL of $CH_2Cl_2$ was added a solution of 0.92 g of Part D alcohol ester in 13 mL of $CH_2Cl_2$. This mixture was stirred under argon at room temperature for 1 hour 50 minutes and then diluted with approximately 125 mL of ethyl ether. The mixture was stirred vigorously for 5 minutes and then filtered through a 1-2 inch pad of Florisil. The filter cake was rinsed with approximately 150 mL of ethyl ether. The combined filtrates were concentrated in vacuo to afford 0.69 g of title aldehyd (75%).

TLC: silica gel, 4% $CH_3OH/CH_2Cl_2$, $R_f$=0.8.

F.
Methyl-[1S-[1α,2β,3β(syn),4α]]-3-[2-[3-[[[(phenylamino)carbonyl]hydrazono]methyl]-7-oxabicyclo[2.2.1]hept-2-yl]ethyl]benzene acetate and

G.
Methyl-[1S-[1α,2β,3β(anti),4α]]-3-[2-[3-[[[(phenylamino)carbonyl]hydrazono]methyl]-7-oxabicyclo[2.2.1]hept-2yl]ethyl]benzene acetate To a stirred solution of 0.69 g of Part E aldehyde (2.28 mmol) in 15 mL of absolute ethanol was added 0.39 g (2.58 mmol) of 4-phenylsemicarbazide (Aldrich). This solution was stirred at room temperature for 17.5 hours and then concentrated in vacuo. The residue was chromatographed on 50 g of silica gel using 2% $CH_3OH/CH_2Cl_2$ to afford 0.18 of title F compound, 0.61 g title G compound and 0.16 g of impure title G compound. The total yield of semicarbazone was 96%.

TLC: silica gel, 2:1 hexane/ether, $R_f$=0.5 of title F compound, 0.35 of title G compound.

H.
[1S-(1α,2β,3β,4α)]-3-[2-[3-[[[(Phenylamino)carbonyl]hydrazono]methyl]-7-oxabicyclo-[2.2.1]hept-2-yl]ethyl]benzeneacetic acid To a stirred solution of 0.5 g of Part G compound in 16 mL of tetrahydrofuran and 1.0 mL of water was added 2.0 mL of 1N LiOH and 1.0 mL of methanol. This mixture was stirred at room temperature for 2 hours at which time TLC analysis showed the reaction to be complete. The pH of the reaction mixture was adjusted to 6-7 by the addition of 6N HCl and the concentrated in vacuo to remove most of the THF. The residue was diluted with 5 mL H₂O, acidified to pH=4, and extracted with CHCl₃ (25 mL, 25 mL, 10 mL). The combined chloroform layers were dried over MgSO₄, filtered and concentrated in vacuo to afford crude title compound. Purification was effected by flash chromatography on 35 g of Silicar CC-7 using 4% $CH_3OH/CH_2Cl_2$ as eluent. This provided 290 mg of a 4:1 anti/syn isomer mixture of title compound and 90 mg of a 3:2 syn/anti mixture of title compound.

TLC: silica gel; 6% $CH_3OH/CH_2Cl_2$, $R_f$×0.33 (anti); $R_f$×0.45 (syn).

¹³C NMR of anti title compound (CDCl₃, 67.5 MHz) δ176.2, 154.5, 146.3, 141.8, 137.6, 134.0, 129.4, 128.8, 128.6, 127.1, 127.0, 123.4, 119.6, 79.9, 79.8, 50.7, 48.0, 41.1, 35.0, 32.2, 29.8, 28.8.

¹³C NMR of syn title compound (CDCl₃, 67.5, MHz) δ176.3, 155.3, 146.1, 137.4, 134.0, 129.5, 128.8, 127.0, 123.6, 123.5, 119.7, 79.6, 47.5, 45.9, 41.0, 34.7, 32.2, 29.8, 28.6.

EXAMPLE 3
[1β,2α,3α,4β]-3-[[3-[[(Phenylmethoxy)-imino]methyl]-7-oxabicyclo[2.2.1]hept-2-yl]-methyl]benzeneacetic acid

A.
[1β,2α,3α,4β]-3-[[-3-[[(Phenylmethoxy)-imino]methyl]-7-oxabicyclo[2.2.1]hept-2-yl]-methyl]benzeneacetic acid, methyl ester Sodium acetate (164 mg, 2 mmol) is added to a magnetically stirred suspension of O-benzylhydroxyl-amine hydrochloride (320 mg, 2 mmol) in ethanol (8 mL) at room temperature. Then, [1β,2α,3α,4β]-3-[[3-formyl-7-oxabicyclo[2.2.1]hept-2-yl]methyl]benzeneacetic acid, methyl ester prepared as described in Example 1, Part F (532 mg, 2 mmol) in ethanol (2 mL) is added and stirred for 1 hour at room temperature. The reaction is poured into ethyl ether (100 mL), which is washed with 1N HCl (20 mL×2), and dried over MgSO₄. Filtration and evaporation of solvents give the title compound which is purified by a silica gel column (silica 60, 30 g) eluted with ethyl ether/petroleum ether to give title compound.

B.
[1β,2α,3α,4β]-3-[[-3-[[(Phenylmethoxyl)-imino]methyl]-7-oxabicyclo[2.2.1]hept-2-yl]-methyl]benzeneacetic acid 1N LiOH (6 mL) is added to the title A ester (1.0 mmol) in tetrahydrofuran (30 mL) and H₂O (6 mL) at room temperature. After 6 hours stirring at room temperature, the reaction is quenched by addition of 1N HCl (6 mL) and poured into brine (20 mL). The products are extracted with ethyl ether (100 ml×3). The combined ether layers are washed with brine (50 mL×3) and dried over Na₂SO₄. Filtration and evaporation of solvent yields title acid, which is purified by a silica gel column eluted with $CH_2Cl_2$/methanol to give the title product.

EXAMPLE 4
[1S-(1α,2β,3β,4α)]-3-[[2-[3-[2-(1-Oxopentyl)-hydrazono]methyl]-7-oxabicyclo[2.2.1]hept-2-yl]ethyl]-benzneacetic acid

A.
[1S-(1α,2β,3β,4α)]-3-[[2-[3-[2-(1-Oxopentyl)hydrazone]methyl]-7-oxabicyclo-[2.2.1]hept-2-yl]ethyl]-benzneacetic acid, methyl ester A solution of the Example 2, Part E aldehyde (532 mg, 2 mmol) and pentanoyl hydrazide (prepared as described in Example 19, Part A of U.S. Pat. No. 4,416,896) (255.1 mg, 2.2 mmol) in ethanol (10 mL) is stirred at room temperature for 2 hours. The reaction mixture is poured into 10 mL of ethyl ether and washed with 1N HCl(2×20 mL), saturated NaHCO₃ solution (2×20 mL) and saturated NaCl solution (2×20 mL). The ether solution is dried over MgSO₄, filtered and freed of solvent in vacuo leaving an oil. This is chromatographed on silica gel 60, eluting with ethyl ether to give title A compound.

B.

[1S-(1α,2β,3β,4α)]-3-[[2-[3-[2-(1-Oxopentyl)hydrazono]methyl]-7-oxabicyclo[2.2.1]-hept-2-yl]ethyl]-benzeneacetic acid Following the procedure of Example 3, Part B but substituting the Part A methyl ester for the Example 3 Part A methyl ester, the title acid product is obtained.

EXAMPLE 5

[1S-(1α,2β,3β,4α)]-3-[[3-[[(Pentyloxy)imino]-methyl]-7-oxabicyclo[2.2.1]hept-2-yl]-methyl]benzeneacetic acid O-Pentylhydroxyamino hydrochloride (prepared as described in Example 22 Parts A–C of U.S. Pat. No. 4,416,896) (306.9 mg, 2.2 mmol) is added to a suspension of sodium acetate (196.8 mg, 2.4 mmol) in dry ethanol (10 mL). NaCl is immediately precipitated out. Then, aldehyde prepared as described in Example 1, Part F (532 mg, 2.0 mmol) in dry ethanol (1 mL) is added at room temperature. After 1 hour stirring, the reaction mixture is poured into ethyl ether, which is washed with 1N HCl(20 mL×2) and dried over MgSO₄. Filtration and evaporation of solvents in vacuo give an oil which is purified by column chromatography (silica 60, 30 g) eluted with ether/petroleum ether to give the methyl ester of the title compound.

1N LiOH (6 mL) is added to the methyl ester (1.0 mmol) in tetrahydrofuran (30 mL) and H₂O (6 mL) at room temperature. After 6 hours stirring at room temperature, the reaction is quenched by addition of 1N HCl (6 mL) and poured into brine (20 mL). The products are extracted with ethyl ether (100 mL×3). The combined ether layers is washed with brine (50 mL×3) and dried over Na₂SO₄. Filtration and evaporation of solvent yield the product which is purified by a silica gel column eluted with CH₂Cl₂/CH₃OH to give the title product.

EXAMPLE 6

[1S-(1α,2β,3β,4α)]-3-[2-[3-[[[(Propoxy)carbonyl]-hydrazono]methyl]-7-oxabicyclo[2.2.1]-hept-2-yl]ethyl]benzeneacetic acid

A.

[1S-(1α,2β,3β,4α)]-3-[2-[3-[[[(Propoxy)-carbonyl]hydrazono]methyl]-7-oxabicyclo-[2.2.1]hept-2-yl]ethyl]-benzeneacetic acid, methyl ester Example 2, Part E aldehyde (2 mmol) and n-propyl hydrazinocarboxylate (prepared by refluxing hydrazine hydrate (1.9 g, 0.038 mol) and di-n-propyl carbonate (5.3 g, 0.036 mol) for 43 hours), 283.2 mg, 2.4 mmol are dissolved in ethanol (10 mL) and is stirred at room temperature for 2 hours. The reaction is concentrated in vacuo leaving an oil which is purified by silica gel column (silica 60, 30 g) eluted with ethyl ester/petroleum ether (3.5/1.5) to give title ester.

B.

[1S-(1α,2β,3β,4α)]-3-[2-[3-[[[(Propoxy)-carbonyl]hydrazono]methyl]-7-oxabicyclo-[2.2.1]hept-3-yl]ethyl]-benzeneacetic acid The title A methyl ester (0.77 mmol) is dissolved in THF (40 mL) and water (7 mL) in an argon atmosphere. While stirring, 1N LiOH solution (7.7 mL) is added and the mixture is stirred at room temperature 4 hours. 1N HCl solution (7.7 mL) is added to adjust the pH to ~6 and the mixture is poured into saturated NaCl column (200 mL). The product is extracted into ethyl acetate (3×100 mL). The combined ethyl acetate extracts are washed with saturated NaCl solution (4×75 mL), dried (MgSO₄) and freed of solvent in vacuo leaving an oil. This is chromatographed on silica gel eluting with CH₃OH in CH₂Cl₂ to give the title product.

EXAMPLE 7

[1S-(1α,2β,3β,4α)]-3-[[3-[[[(Phenylamino)-thiocarbonyl]hydrazono]methyl]-7-oxabicyclo[2.2.1]-hept-2-yl]methyl]benzeneacetic acid Following Example 1, Parts G and H, except substituting 4phenylthiosemicarbazide for 4-phenyl-semicarbazide in Part G, the title acid is obtained.

EXAMPLES 8 TO 25

Examples of additional compounds in accordance with the present invention which may be prepared following the procedures outlined in the specification and working Examples and in U.S. Pat. No. 4,416,896 include, but are not limited to, the following:

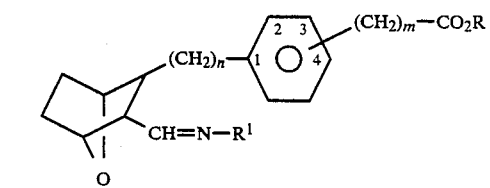

| Ex. No. | n | (CH₂)ₘ—CO₂R (position) | R¹ |
|---|---|---|---|
| 8 | 1 | CH₂—CO₂H (4) | OCH₃ |
| 9 | 2 | (CH₂)₂—CO₂H (2) | OC₆H₅ |
| 10 | 1 | (CH₂)₂—CO₂H (2) | O<br>‖<br>OCCH₃ |

-continued

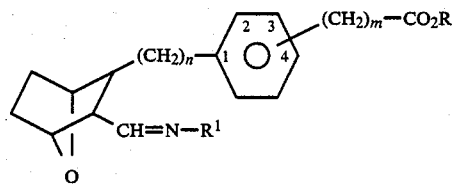

| Ex. No. | n | (CH$_2$)$_m$—CO$_2$R (position) | R$^1$ |
|---|---|---|---|
| 11 | 2 | CH$_2$—CO$_2$Li (2) | —OC(=O)C$_6$H$_5$ |
| 12 | 1 | (CH$_2$)$_2$—CO$_2$Na (3) | —N(H)—C(=O)—C$_2$H$_5$ |
| 13 | 2 | CH$_2$CO$_2$CH$_3$ (2) | —N(H)—C(=O)—C$_6$H$_5$ |
| 14 | 1 | (CH$_2$)$_2$CO$_2$C$_2$H$_5$ (4) | —N(H)—C(=O)—OCH$_3$ |
| 15 | 2 | CH$_2$CO$_2$H (4) | —N(H)—C(=O)—OC$_6$H$_5$ |
| 16 | 1 | CH$_2$CO$_2$H (3) | —N(H)—C(=O)—N(H)—C$_4$H$_8$—cyclo C$_6$H$_{12}$ |
| 17 | 2 | CH$_2$CO$_2$H (2) | —N(H)—C(=O)—N(H)—C$_6$H$_5$ |
| 18 | 1 | (CH$_2$)$_2$CO$_2$CH$_3$ (2) | —N(H)—C(=O)—N(H)—C$_6$H$_{13}$ |
| 19 | 1 | CH$_2$CO$_2$Li (3) | —N(H)—C(=S)—N(H)—(CH$_2$)$_4$—C$_6$H$_5$ |
| 20 | 1 | (CH$_2$)$_2$CO$_2$Na (2) | —N(H)—C(=S)—N(H)—C$_4$H$_9$ |
| 21 | 2 | CH$_2$CO$_2$H (3) | —N(H)—C(=S)—N(H)—C$_6$H$_5$ |
| 22 | 1 | (CH$_2$)$_2$CO$_2$H (3) | —N(H)—C(=S)—N(H)—C$_3$H$_7$ |
| 23 | 2 | CH$_2$CO$_2$H (4) | —N(H)—C(=S)—N(H)—CH$_2$—C$_6$H$_5$ |
| 24 | 1 | CH$_2$CO$_2$H (2) | —N(H)—C(=S)—N(H)—CH$_2$—C$_6$H$_5$ |
| 25 | 1 | CH$_2$CO$_2$H (3) | —N(H)—C(=O)—N(H)—CH$_2$C$_6$H$_5$ |

What is claimed is:
1. A compound having the formula

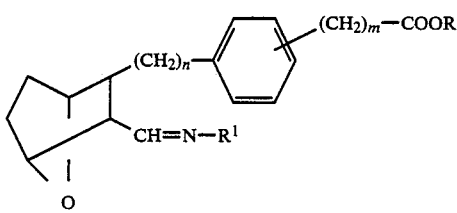

including all stereoisomers thereof, wherein
n is 1 or 2; m is 1 or 2;
R is H, alkali metal or lower alkyl; and
R¹ is —OR²,

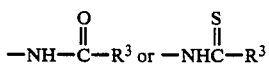

wherein

R² is lower alkyl, aryl, aralkyl, cycloalkylalkyl, alkanoyl or aroyl and

R³ is lower alkyl, aryl, aralkyl, alkoxy, aryloxy, aralkoxy, alkylamino, arylamino, cycloalkylalkylamino or aralkylamino;

wherein lower alkyl or alkyl by itself or as part of another group may be unsubstituted or substituted with halo, alkoxy, aryl, alkyl-aryl, haloaryl, cycloalkyl or alkylcycloalkyl;

aryl by itself or as part of another group may be unsubstituted or substituted with 1 or 2 lower alkyl groups, 1 or 2 halogens and/or 1 or 2 lower alkoxy groups;

cycloalkyl by itself or as part of another group may be unsubstituted or substituted with 1 or 2 halogens, 1 or 2 lower alkyl groups and/or 1 or 2 lower alkoxy groups.

2. The compound as defined in claim 1 having the formula

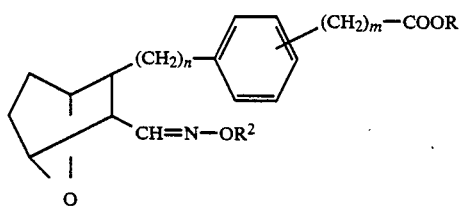

3. The compound as defined in claim 1 having the formula

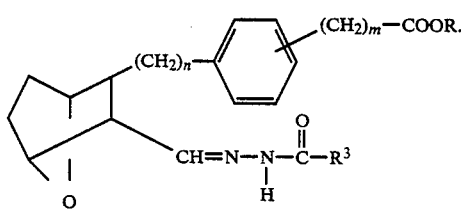

4. The compound as defined in claim 1 having the formula

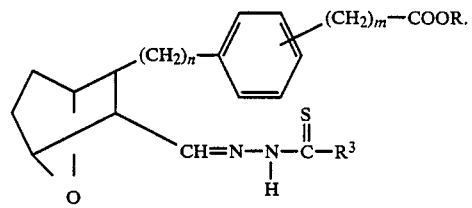

5. The compound as defined in claim 1 wherein —(CH₂)ₘ—COOR is in the meta-position.

6. The compound as defined in claim 1 wherein —(CH₂)ₘ—COOR is in the ortho-position.

7. The compound as defined in claim 3 having the formula

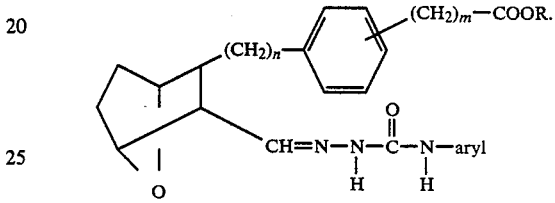

8. The compound as defined in claim 6 having the formula

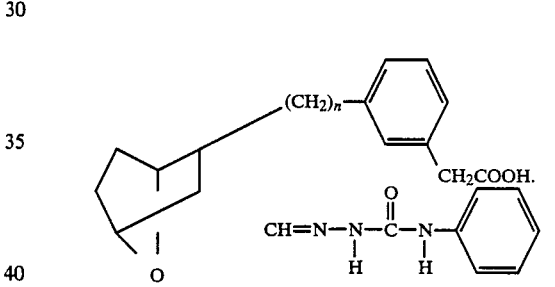

9. The compound as defined in claim 7 having the name [1S-(1α, 2β, 3β,4α)]-3-[[3-[[[(phenylamino)carbonyl]hydrazono]methyl-7-oxabicyclo[2.2.1]-hept-2yl]methyl]benzeneacetic acid.

10. The compound as defined in claim 7 having the name [1S-(1α,2β,3β,4α)]-3-[2-[3-[[[(phenylamino)carbonyl]hydrazono]methyl]-7-oxabicyclo[2.2.1]-hept-2-yl]ethyl]benzeneacetic acid.

11. A composition for inhibiting platelet aggregation and bronchoconstriction comprising an effective amount of a compound as defined in claim 1 and a pharmaceutically acceptable carrier thereof.

12. A method of inhibiting platelet aggregation and bronchoconstriction, which comprises administering to the circulatory system of a mammalian host an effective amount of a compound as defined in claim 1.

13. The method as defined in claim 12 wherein said compound is administered in an amount within the range of from about 1 to about 100 mg/kg.

14. A method of inhibiting platelet aggregation, which comprises administering to a mammalian host an effective amount of a compound as defined in claim 1.

15. A method of inhibiting bronchoconstriction associated with asthma, which comprises administering to a mammalian host an effective amount of a compound as defined in claim 1.

16. A method for improving post-ischemic myocardial dysfunction, which comprises administering to a mammalian host in need of such treatment an effective amount of a compound as defined in claim 1.

17. A method for preventing or reducing platelet loss during extracorporeal circulation, which comprises administering to a mammalian host in need of such treatment an effective amount of a compound as defined in claim 1.

18. A method for preventing or reducing venous thrombosis which comprises administering to a mammalian host in need of such treatment an effective amount of a compound as defined in claim 1.

19. A method for treating burn injuries and/or promoting wound healing, which comprises administering to a mammalian host in need of such treatment an effective amount of a compound as defined in claim 1 in systemic or topical form.

20. A method for treating migraine headaches, which comprises administering to a mammalian host in need of such treatment an effective amount of a compound as defined in claim 1.

* * * * *